United States Patent
Bloemer et al.

(10) Patent No.: US 6,289,719 B1
(45) Date of Patent: Sep. 18, 2001

(54) METHOD FOR OPERATING A GAS SENSOR

(75) Inventors: Bernhard Bloemer, Stuttgart; Bernd Schumann, Rutesheim, both of (DE)

(73) Assignee: Robert Bosch Gmbh, Stuttgart (DE)

( * ) Notice: Subject to any disclaimer, the term of this patent is extended or adjusted under 35 U.S.C. 154(b) by 0 days.

(21) Appl. No.: 09/308,995

(22) PCT Filed: Oct. 2, 1998

(86) PCT No.: PCT/DE98/02930

§ 371 Date: Jun. 1, 1999

§ 102(e) Date: Jun. 1, 1999

(87) PCT Pub. No.: WO99/18429

PCT Pub. Date: Apr. 15, 1999

(30) Foreign Application Priority Data

Oct. 2, 1997 (DE) .............................. 197 43 644

(51) Int. Cl.[7] ................. F02B 3/00; F02M 7/00
(52) U.S. Cl. ............ 73/23.21; 73/23.31; 73/25.01; 73/31.05; 204/424
(58) Field of Search .................. 73/23.21, 23.31, 73/23.32, 25.03, 25.05, 25.01, 31.05; 204/424

(56) References Cited

U.S. PATENT DOCUMENTS

| 4,332,225 | 6/1982 | Cox et al. . |
| 4,787,966 | 11/1988 | Nakajima et al. . |
| 4,817,414 | * 4/1989 | Hagen et al. ................ 73/23.31 |
| 4,896,143 | * 1/1990 | Dolnick et al. .............. 73/25.03 |
| 4,944,035 | * 7/1990 | Aagardl et al. .............. 73/25.03 |
| 5,054,452 | 10/1991 | Denz . |
| 5,515,714 | * 5/1996 | Sultan et al. ................. 73/25.01 |
| 5,759,366 | * 6/1998 | Ottlinger et al. ............ 204/424 |
| 6,045,673 | * 4/2000 | Kato et al. .................. 204/423 |

FOREIGN PATENT DOCUMENTS

0123842 * 5/1991 (JP) .

* cited by examiner

Primary Examiner—Daniel S. Larkin
Assistant Examiner—Michael Cygan
(74) Attorney, Agent, or Firm—Walter Ottesen

(57) ABSTRACT

A method of operating a gas sensor having two sensor electrodes whose output signal is evaluated in an evaluation circuit connected downstream of the sensor electrodes, the sensor electrodes being arranged in an ion-conducting ceramic and being therefor heated by an electrical heater, characterized in that a pulsewidth modulated heater voltage signal is applied to the heater; and that a compensation signal is superposed on the output signal of the sensor electrodes, the compensation signal being essentially formed so as to be counterclocked and inverted to the pulsewidth modulated heater voltage signal.

7 Claims, 4 Drawing Sheets

METHOD FOR OPERATING A GAS SENSOR

FIELD OF THE INVENTION

The invention relates to a method for operating a gas sensor having two sensor electrodes mounted in an ion-conducting ceramic which is heatable by an electric heater. The output signals of the sensor electrodes are evaluated in an evaluation circuit connected downstream of the sensor electrodes.

BACKGROUND OF THE INVENTION

Such ceramic gas sensors have been known for a long time. These gas sensors are used for detecting toxic exhaust gases, for example, of automobile exhaust gases or burner exhaust gases. The ion-conducting ceramic must be heated for ensuring a proper function and this ceramic can, for example, be zircon oxide ($ZrO_2$). The heater is embedded in an insulating layer which, in most cases, comprises aluminum oxide ($Al_2O_3$). The insulation of the heater is, however, problematic especially at high temperatures because leakage resistances occur from the heater to the sensor electrodes in the order of magnitude of several megaohms. In this case, the leakage current, which flows from the heater, is superposed on the actual measuring current and causes relatively large errors. This is so because in gas sensors of this type, the measuring result lies only at a few microamperes.

Furthermore, in gas sensors, there is a large scattering thereof and a significant deterioration occurs. For this reason, the leakage current cannot be compensated simply by a fixed corrective quantity.

For this reason, it is, for example, known to use an insulating amplifier for measuring the measurement current. With this insulating amplifier, the actual measurement circuit is operated so as to be separated with respect to potential and the measurement quantity is transmitted in an insulated manner for further signal processing. The potential separation can, for example, be achieved via transformers or optoelectronically. In this case, the leakage current cannot flow off and therefore vanishes. As a consequence of this, only the wanted measurement current is measured. The high requirement of expensive and non-integratable components or components which are only integratable with difficulty is disadvantageous.

Furthermore, a method and an arrangement for detecting a fault state of a λ-probe and the measures taken as a consequence of a fault signal are presented in EP 0 403 615 B1. This fault signal is outputted for a detected fault state. In the method, impermissibly large fault causes are diagnosed by a correlation method during operation of the λ-probe. Shunt currents exist only during operation of the heater. For this reason, the probe heater is switched off in this measuring method for detecting a fault state because, in this case, no shunt voltage and therefore no incorrectness of the measuring result is present. The difference between the probe voltage, which is measured for a switched-on heater and a switched-off heater, yields the shunt voltage. This method is relatively complex and requires a rather complex circuit.

SUMMARY OF THE INVENTION

The invention is therefore based on the object to provide a method for operating a gas sensor with a precision of detection of the measurement current as precise as possible with the least amount technical complexity, that is, a method which makes possible a very substantial elimination of a disturbance caused by a leakage current.

The object is achieved in a method for operating a gas sensor of the kind described above in that a pulsewidth modulated heater voltage signal is applied to the heater and that a compensation signal is superposed on the output signal of the sensor electrodes. The compensation signal is essentially counterclocked (inverted) to the pulsewidth modulated heater voltage signal.

One can eliminate the disturbance signal in an especially simple manner by applying a pulsewidth modulated heater voltage signal and by superposing a compensation signal on the output signal of the sensor electrode which defines essentially a counterclocked signal to the pulsewidth modulated heater voltage signal. The disturbance signal is coupled to the sensor signal via the heater voltage. This disturbance signal has essentially the shape of the pulsewidth modulated heater voltage signal with capacitive in-coupling peaks and is substantially compensated by the compensating signal which is formed as a counterclocked signal, that is, as an inverse signal to this heater voltage signal.

The superposition of the compensation signal can, in principle, take place in the most different way. An advantageous embodiment provides that the compensation signal is superposed on the output signal before this output signal is supplied to the evaluation circuit. In this case, the superposition takes place in a manner easy to realize with analog circuitry and one need only process an already compensated signal in the evaluation circuit.

In another advantageous embodiment, it is provided that the compensation signal is superposed on the output signal of the evaluation circuit. In this case, the superposition can likewise be superposed, that is, added with analog circuitry in a simple manner.

In a further advantageous embodiment, it is provided that the compensation signal is superposed on the sensor signal in the evaluation circuit, preferably digitally. This embodiment has especially the advantage that the evaluation circuit, which is anyway present, can be utilized for processing the compensation signal so that additional circuit components for superposing the compensation signal are not required.

So far, no details have been given with respect to the pulsewidth modulated heater voltage. An especially advantageous embodiment provides that the pulsewidth modulated heater voltage signal has flat flanks. This advantageous embodiment especially makes possible a further reduction of the disturbance signal. Because of these flat flanks of the pulsewidth modulated heater voltage signal or, stated otherwise, because the pulsewidth modulated heater voltage with flat flanks is clocked, high frequencies are avoided in the heater voltage signal which could lead to disturbances. This is explained in greater detail below. The flat flanks are slowly increasing and slowly falling flanks of the pulsewidth modulated heater voltage signal.

The generation of a heater voltage signal of this kind having flat flanks can take place in the most different ways. An advantageous embodiment provides that the pulsewidth modulated heater voltage signal with flat flanks is generated by a MOSFET switch having a gate input line. A series resistor is connected in this input line. An RC-lowpass is formed by this series resistor in the gate input line together with the gate capacitors. The RC-lowpass makes possible a slow switching of the pulsewidth modulated heater voltage signal and therefore a reduction of the high frequency components in the signal.

BRIEF DESCRIPTION OF THE DRAWINGS

The invention will now be described with reference to the drawings wherein.

DESCRIPTION OF THE PREFERRED EMBODIMENTS OF THE INVENTION

Figure 4:
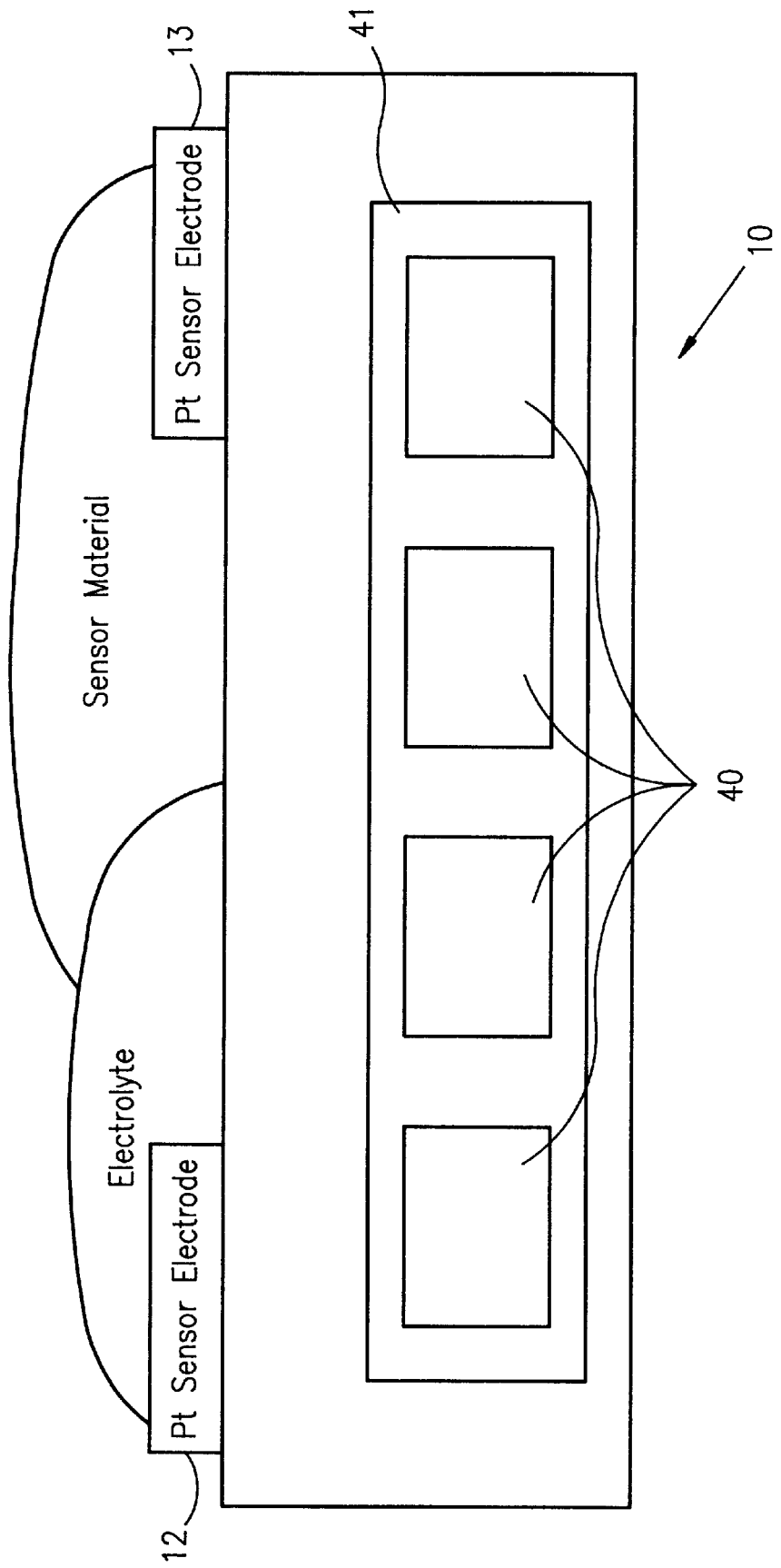

A gas sensor, which is shown schematically in FIG. 4, is for detecting, for example, CO, NO, hydrocarbons or other exhaust gases and includes two sensor electrodes (12, 13). One sensor electrode is embedded in an electrolyte, for example, zircon oxide $ZrO_2$ and the other electrode is embedded in a sensor material, for example, doped titanium oxide. The gas sensor must be heated by a heater 40 for a proper operation thereof. The heater 40 is meander shaped and embedded in an insulating layer 41 comprising, for example, $Al_2O_3$. In the embodiment shown in FIG. 4, the carrier is made, for example, of zirconium oxide and the aluminum oxide layer 41, in which the heater is embedded, is generated, for example, by silk-screen techniques.

Furthermore, the carrier itself can be made of aluminum oxide $Al_2O_3$. It is understood that in this case any embedding of the heater is unnecessary because $Al_2O_3$ is non-conductive.

The heater cannot be completely insulated especially at high temperatures at which, in addition, the conductivity of the zirconium oxide increases. For this reason, disturbances occur because of in-coupling of the heater voltage in the sensor signal. The in-coupling is caused by a residual conductivity in the ceramic substrate which is based on ion conduction or electron conduction or because of a residual conductivity in the electrolyte layer and the sensor material layer.

Figure 1:
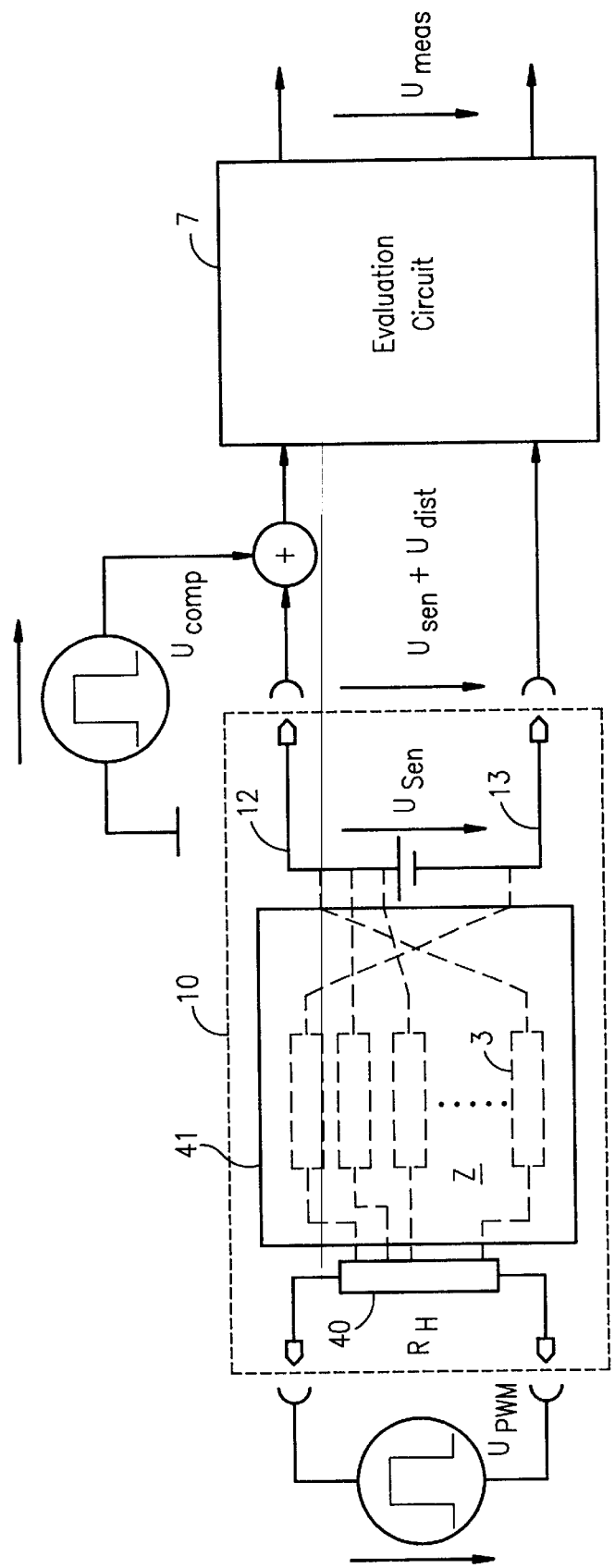
FIG. 1 schematically shows a first embodiment of a method of the invention for operating a gas sensor based on a circuit to operate the gas sensor.
Figure 2:
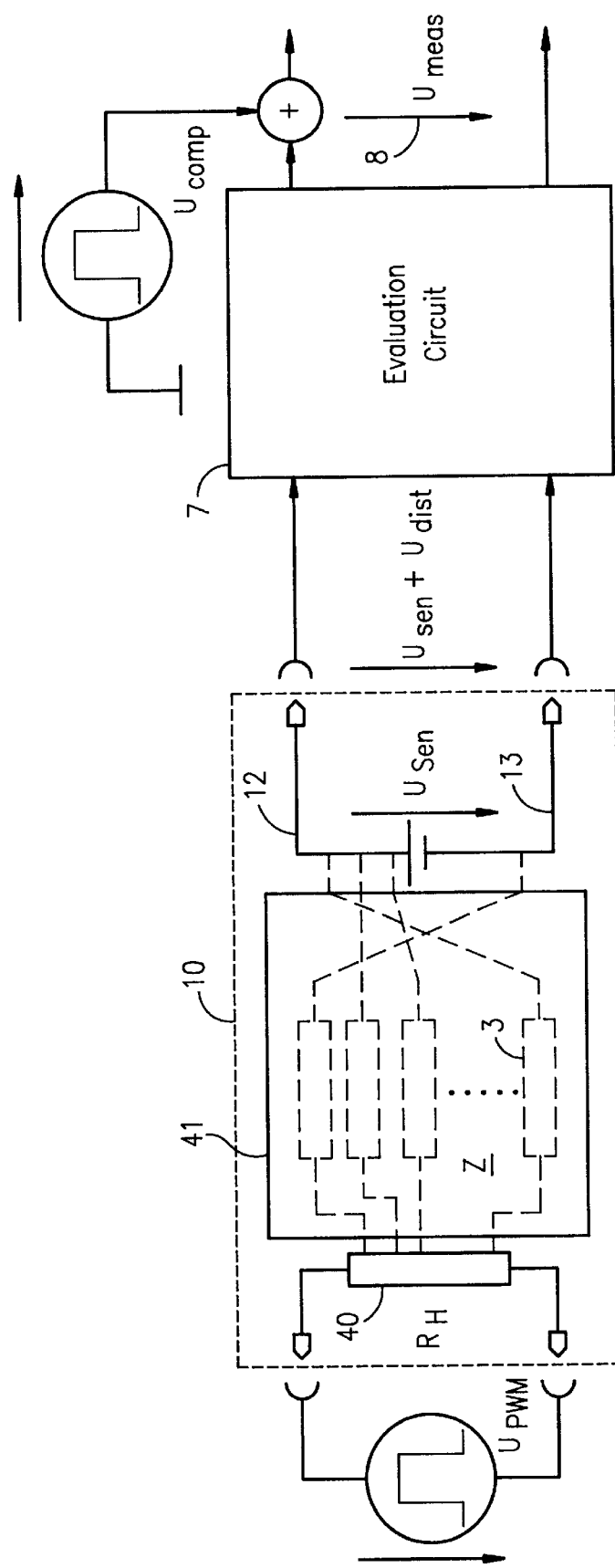
FIG. 2 shows another embodiment of the method of the invention for operating a gas sensor with reference to a circuit for operating the gas sensor.
Figure 3:
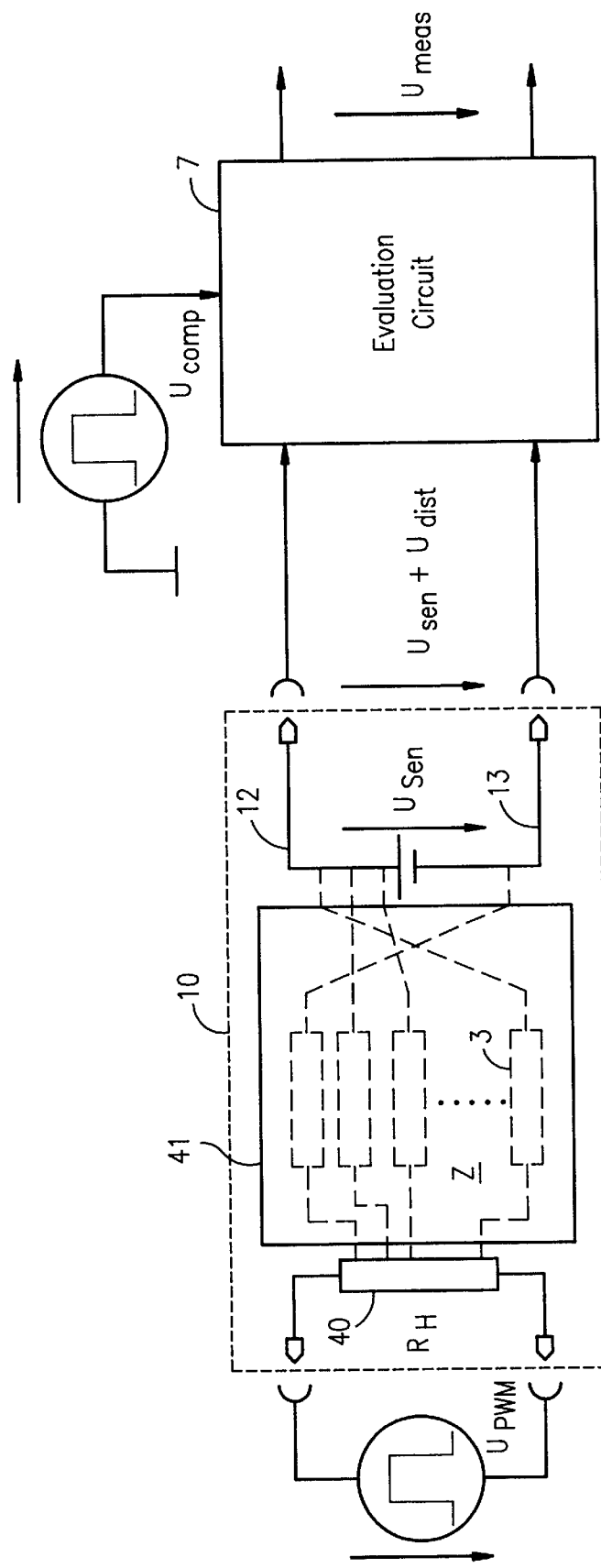
FIG. 3, in turn, shows another embodiment of the method for operating a gas sensor with respect to a circuit for operating the gas sensor; and, FIG. 4 is a schematic of a known gas sensor.

A circuit for operating a gas sensor is shown schematically in FIGS. 1 to 3. In this illustration, the heater 40 is shown as resistance $R_H$. The sensor signal $U_{sen}$ is tapped at the sensor electrodes (12, 13) and a disturbance signal $U_{dist}$ is superposed on the sensor signal. The disturbance signal $U_{dist}$ arises by in-coupling of the heater voltage as described above. The disturbance can be schematically illustrated as shown in FIGS. 1 to 3 by a finite parasitic impedance Z. This impedance Z is defined by an infinite number of individual impedances schematically shown by resistors 3 shown in phantom outline. The heater couples disturbance voltages to different locations of the sensor electrodes (12, 13) via these resistances 3 so that the disturbance signal $U_{dist}$ is superposed on the actual sensor signal $U_{sen}$: $U_{sen} + U_{dist}$. This signal is processed in an evaluation circuit 7 which outputs a measurement signal $U_{meas}$ for further processing.

The following is done in order to minimize the disturbances described above as much as possible.

A pulsewidth modulated signal $U_{PWM}$ is applied to the heater and a compensating signal $U_{comp}$ is superposed on the output signal $U_{sen}$ of the sensor electrodes. The compensating signal $U_{comp}$ is essentially configured to be inverted to the pulsewidth modulated heater voltage signal $U_{PWM}$. The disturbance component of the signal $U_{dist}$ is reduced by this superposition. As shown in FIG. 1, the superposition can take place forward of the evaluation circuit 7 by addition of the compensating signal $U_{comp}$.

The compensation signal is superposed on the output signal of the evaluation circuit by addition in the circuit shown in FIG. 2.

The superposition takes place in these two cases in an analog manner.

In the embodiment shown in FIG. 3, the compensation signal is shown superposed digitally in the evaluation circuit of the sensor signal 7. In this case, no additional circuit components are required. The superposition of the compensation signal takes place as an integral part of the evaluation circuit 7 which, for example, can contain a microcomputer so that the superposition can take place with a program.

Furthermore, the pulsewidth modulated heater voltage signal is so configured that it has flat flanks, that is, flanks which increase and decrease slowly in dependence upon time. Such slowly increasing and decreasing flanks have a lower high frequency component, which causes reduced disturbances when compared to rapidly increasing and falling flanks (Fourier analysis). The capacitive part of the parasitic impedance Z has low ohmage at higher frequency and therefore is better conductive for the disturbance signal. For this reason, higher frequencies in the heater voltage signal $U_{PWM}$ should be avoided to minimize the disturbance voltage.

The pulsewidth modulated heater voltage signal $U_{PWM}$ can, for example, be clocked with the aid of a MOSFET switch. In this case, a series resistance is provided in the gate input line of the MOSFET switch which, together with the gate capacitance, forms a RC-lowpass. This lowpass effects a slow switching of the pulsewidth modulated heater voltage and therefore reduces the high frequency components in the signal.

Disturbance signals are minimized with a relatively low technical complexity with the method described above. This is especially so for very low sensor currents which occur for especially low gas concentrations. In this way, the detection of the sensor signal $U_{sen}$ is simplified or even made possible.

What is claimed is:

1. A method for operating a gas sensor having two sensor electrodes and supplying an output signal ($U_{sen}$) thereacross, the gas sensor including: an ion conducting ceramic and said sensor electrodes being disposed therein; and, an electric heater for heating said ceramic and said sensor electrodes to ensure proper operation of said gas sensor, said electric heater being electrically insulated from said sensor electrodes with leakage resistances being present between said heater and said sensor electrodes in an order of magnitude of several megaohms at high temperatures whereby an unwanted electrical leakage current flows from said heater to said sensor electrodes when said electric heater is energized, the method comprising the steps of:

connecting an evaluation circuit downstream of said sensor electrodes for evaluating said output signal ($U_{sen}$) with said unwanted leakage current being superposed thereon causing errors;

applying a pulsewidth modulated heater voltage signal ($U_{PWM}$) to said heater;

superposing a compensation signal ($U_{comp}$) on said output signal ($U_{sen}$) of said sensor electrodes; and, forming said compensation signal ($U_{comp}$) so as to be counterclocked and inverted to said pulsewidth modulated heater voltage signal ($U_{PWM}$) to compensate said unwanted leakage current thereby correcting said errors.

2. The method of claim 1, comprising the further step of: superposing said compensating signal ($U_{comp}$) on said output signal ($U_{sen}$) of said sensor electrodes before said output signal ($U_{sen}$) is supplied to said evaluation circuit.

3. The method of claim 1, wherein said evaluation circuit outputs an output signal; and, the method comprising the further step of superposing said compensation signal ($U_{comp}$) on said output signal of said evaluation circuit.

4. The method of claim 1, comprising the further step of superposing said compensation signal ($U_{comp}$) on the sensor signal ($U_{sen}$) in the evaluation circuit.

5. The method of claim 4, wherein said compensation signal ($U_{comp}$) is digitally superposed on said sensor signal ($U_{sen}$).

6. The method of claim 1, wherein said pulsewidth modulated heater voltage signal ($U_{PWM}$) has slowly rising and slowly falling flanks.

7. The method claim 6, comprising the further step of generating said pulsewidth modulated heater voltage signal ($U_{PWM}$) with a MOSFET switch having a gate input line including a series resistor.

* * * * *